United States Patent [19]
Salyer

[11] Patent Number: 5,477,917
[45] Date of Patent: Dec. 26, 1995

[54] DRY POWDER MIXES COMPRISING PHASE CHANGE MATERIALS

[75] Inventor: Ival O. Salyer, Dayton, Ohio

[73] Assignee: The University of Dayton, Dayton, Ohio

[21] Appl. No.: 315,256

[22] Filed: Sep. 29, 1994

Related U.S. Application Data

[63] Continuation of Ser. No. 44,819, Apr. 8, 1993, Pat. No. 5,370,814, which is a continuation-in-part of Ser. No. 870,487, Apr. 16, 1992, Pat. No. 5,282,994, which is a continuation-in-part of Ser. No. 462,365, Jan. 9, 1990, Pat. No. 5,106,520.

[51] Int. Cl.⁶ ........................................................ C09K 5/06
[52] U.S. Cl. .................... 165/104.26; 252/77; 252/73; 220/429
[58] Field of Search .................... 252/77, 73, 71; 165/104.26; 220/429

[56] References Cited

U.S. PATENT DOCUMENTS

| | | | |
|---|---|---|---|
| 2,959,671 | 11/1960 | Stevinson | 250/17 |
| 3,559,594 | 2/1971 | Miller | 109/84 |
| 3,823,089 | 7/1974 | Ryan | 252/70 |
| 3,823,769 | 7/1974 | Anderson et al. | 165/104.26 X |
| 3,977,202 | 8/1976 | Forusz | 62/4 |
| 3,980,070 | 9/1976 | Krupa | 126/263 |
| 4,003,426 | 1/1977 | Best | 252/20 |
| 4,008,170 | 2/1977 | Allan | 428/318 |
| 4,182,398 | 1/1980 | Salyer | 252/70 |
| 4,205,685 | 6/1980 | Yoshida | 52/173 |
| 4,237,023 | 12/1980 | Johnson | 252/70 |
| 4,253,983 | 3/1981 | Blanie | 252/70 |
| 4,259,198 | 3/1981 | Kreibich | 252/70 |
| 4,259,401 | 3/1981 | Chahroudi | 428/306 |
| 4,273,667 | 6/1981 | Kent et al. | 252/70 |
| 4,292,189 | 9/1981 | Chen | 252/70 |
| 4,294,078 | 10/1981 | MacCracken | 62/59 |
| 4,367,788 | 1/1983 | Cordon | 165/53 |
| 4,463,799 | 8/1984 | Takahashi et al. | 165/10 |
| 4,470,917 | 9/1984 | Hawe et al. | 252/70 |
| 4,504,402 | 3/1985 | Chen et al. | 252/70 |
| 4,505,953 | 3/1985 | Chen et al. | 427/212 |
| 4,513,053 | 4/1985 | Chen et al. | 428/221 |
| 4,545,916 | 10/1985 | Chalk et al. | 252/70 |
| 4,561,989 | 12/1985 | Wada et al. | 252/70 |
| 4,567,877 | 2/1986 | Sepahpur | 126/246 |
| 4,603,106 | 9/1986 | Ryan et al. | 62/457 |
| 4,617,332 | 10/1986 | Salyer et al. | 252/70 |
| 4,668,564 | 5/1987 | Orchard | 428/246 |
| 4,671,267 | 6/1987 | Stout | 128/156 |
| 4,680,173 | 7/1987 | Burger | 424/47 |
| 4,694,119 | 9/1987 | Groenewegen | 174/52 PG |
| 4,711,813 | 12/1987 | Salyer | 428/402 |

(List continued on next page.)

FOREIGN PATENT DOCUMENTS

| | | |
|---|---|---|
| 0022717 | 1/1981 | European Pat. Off. . |
| 197806 | 6/1978 | France . |
| 2643895 | 3/1978 | Germany . |
| 3045842 | 7/1982 | Germany . |
| 42380 | 4/1979 | Japan . |
| 1422767 | 8/1984 | Japan . |
| 1701180 | 9/1984 | Japan . |
| 232164 | 12/1984 | Japan . |
| 86188 | 5/1985 | Japan . |
| 86191 | 5/1985 | Japan . |

*Primary Examiner*—John Rivell
*Assistant Examiner*—Christopher Atkinson
*Attorney, Agent, or Firm*—Killworth, Gottman, Hagan & Schaeff

[57] ABSTRACT

A free flowing, conformable powder-like mix of silica particles and a phase change material (PCM) is provided. The silica particles have a critical size of about 0.005 to about 0.025 microns and the PCM must be added to the silica in an amount of 75% or less PCM per combined weight of silica and PCM. The powder-like mix can be used in tableware items, medical wraps, tree wraps, garments, quilts and blankets, and particularly in applications for heat protection for heat sensitive items, such as aircraft flight recorders, and for preventing brake fade in automobiles, buses, trucks and aircraft.

20 Claims, 3 Drawing Sheets

U.S. PATENT DOCUMENTS

| | | | |
|---|---|---|---|
| 4,721,227 | 1/1988 | Hughes et al. | 220/429 |
| 4,747,240 | 5/1988 | Voisinet et al. | 52/173 |
| 4,851,291 | 7/1989 | Vigo et al. | 428/393 |
| 4,893,397 | 1/1990 | Hughes | 29/428 |
| 4,944,401 | 7/1990 | Groenewegen | 206/521 |
| 4,964,402 | 10/1990 | Grim | 128/80 H |
| 5,106,520 | 4/1992 | Salyer | 252/70 |

DRY POWDER MIXES COMPRISING PHASE CHANGE MATERIALS

GOVERNMENT RIGHTS

The Government has rights in this invention pursuant to Contract No. DE-FG03-86SF16308 awarded by the U.S. Department of Energy.

RELATED APPLICATIONS

This application is a continuation of application Ser. No. 08/044,819, filed Apr. 8, 1993, now U.S. Pat. No. 5,370,814, which is a continuation-in-part of Ser. No. 870,487, filed Apr. 16, 1992 now U.S. Pat. No. 5,282,994, which is a continuation-in-part of Ser. No. 462,365, filed Jan. 9, 1990, now U.S. Pat. No. 5,106,520. The disclosures of U.S. patent application Ser. Nos. 870,487 and 462,365 are hereby incorporated by reference. Reference is also made to related application Ser. No. 835,854, filed Feb. 18, 1992 as a divisional of Ser. No. 462,365.

BACKGROUND OF THE INVENTION

The present invention relates to a dry, freely flowing powder mix comprising a phase change material.

Phase change materials may be repeatedly converted between solid and liquid phases and utilize their latent heats of fusion to absorb, store and release energy to heat or cool during such phase conversions. Phase change materials may also be converted from a liquid to a gas and utilize their latent heats of vaporization and condensation to absorb and release energy in the form of heat for purposes of temperature control.

In phase change materials, the amount of energy absorbed upon melting or vaporizing, or released upon freezing and condensation is much greater than the amount of energy absorbed or released upon increasing or decreasing the temperature of the material over an increment of 1° C.

Upon melting, freezing, vaporizing and condensing, per unit weight, a phase change material (PCM) absorbs or releases substantially more energy than a sensible heat storage material that is heated or cooled in generally the same temperature range. In contrast to a sensible heat storage material that absorbs and releases energy essentially uniformly over a broad temperature range, a phase change material absorbs and releases a large quantity of energy in the vicinity of its melting/freezing point, and an even greater quantity of energy in the vicinity of its boiling and condensation point.

Typical phase change materials of the solid-to-liquid type can store and release 40 to 80 calories per gram of phase change material. The liquid-to-gas change of state for phase change materials is generally six times as energetic as the solid-to-liquid transition (e.g., ice to water, 80 cal/g; water to steam, >500 cal/g). However, the much more energetic liquid-to-gas transition has been little used for conventional temperature control purposes because of the large volume and pressure changes that normally accompany it, which changes can be especially problematic in closed environments.

Phase change materials capable of storing and releasing thermal energy have found many applications in building structures, road base materials, beverage and food containers, medical wraps, and textile applications such as garments. One of the basic problems, however, in the use of solid-to-liquid PCM's for control of temperature, is containment. That is, for heat transfer efficiency as well as safety purposes, it is undesirable to have a thick block or agglomeration of solid phase PCM below the PCM melting point. Similarly, when above the melting point, PCM in liquid phase can be problematic. For instance, building panels containing liquid phase PCM have proven deficient. In one such PCM-containing panel, carpenters reported that a liquid phase PCM leaked out of the panel when nails were driven through it. Additionally, the volume changes that accompany melting and freezing can cause problems in breaking the containing vessel unless adequate provisions are made to accommodate the volume changes. Most phase change materials expand ~10% in melting. Water however expands ~10% in freezing.

In those situations in which medical hot or cold packs containing PCMs are used, a solid phase agglomerate of PCM below its melting point renders the structure unwieldy and incapable of conforming about the required body part to achieve the desired heating or cooling function.

Accordingly applicant has developed a series of PCM containment systems. These are represented by U.S. Pat. Nos. 4,617,332, 4,711,813, 4,797,160, 4,908,166, and 5,053, 446, all assigned to the same assignee as the present invention. However, none of the containment means disclosed in those patents involve silica. Still, the broad idea of using silica as a suspension medium for PCMs in building blocks is not new. For instance, see U.S. Pat. No. 4,259,401 (Charoudi et al) wherein this concept is disclosed at column 21, line 60 et seq. Also, Johnson et al in U.S. Pat. No. 4,237,023 discloses incorporating fumed silicon dioxide with inorganic phase-change salts which are capable of forming salt hydrates in the presence of water and Chang in U.S. Pat. No. 4,292,189 discloses a phase change energy storage system based on a combination of two inorganic salts together with nucleating and thickening agents including silicas. Finally, Allen, U.S. Pat. No. 4,008,170 describes a powdered product prepared by the vapor phase hydrolysis of a silicon compound reacted with liquid water. However, the dry water in Allen is not used as a phase change material for the storing and releasing of thermal energy.

The prior art does not suggest utilization of the combination of the preferred silica having the recited particle size and the PCM/silica weight ratios herein required in order to result in a dry, conformable, powder-like, PCM containing composition that may be useful in widespread environments.

SUMMARY OF THE INVENTION

The present invention provides a novel phase change material/silica dry powder composite. When solid-to-liquid transitions are contemplated, the phase change material (PCM) may consist of one or more of the following compositions: water, salt hydrates, quaternary ammonium halide clathrates, linear alkyl hydrocarbons, fatty acids, alcohols and esters, glycerine, pentaerythritol, pentaglycerine, neopentylglycol, polyethylene glycol and like materials characterized by having thermal energy storage of 30 calories/ gram or higher, and a narrow temperature range of melting and freezing. When liquid-to-gas transitions are contemplated, the preferred phase change materials are water, ethylene glycol, combinations of water and ethylene glycol, glycerol, combinations of water/glycerol, water/ethylene glycol/glycerin, methanol, dimethylformamide, and like materials.

The silicas that are suitable include those made by the fumed or precipitated process, and having surface areas ranging from 50 to 500 square meters per gram, and primary particle sizes from 0.005 to 0.046 microns. Preferred silicas are those having a surface area of 100 $m^2$ per gram or more, and primary particle size of 0.025 microns or less. Further, the silicas prepared by either the fumed or precipitated process can be modified to make them less hydrophilic, or even hydrophobic by surface treating them with effective concentrations of silane coupling agents (e.g., dimethyldichlorosilane) or silicone resins. The silicone resin surface treatment can and usually is followed by heat treating at elevated temperature wherein the silicone resin is chemically reacted with hydroxyl groups on the surface of the silica particles. Importantly, controlled degrees of hydrophobic character can be obtained by varying the amount of waterproofing agent. This precisely tailored balance of hydrophobic/hydrophilic character is very important in the preparation of PCM/silica dry powders using quaternary ammonium halides, and salt hydrates in order to diminish the attraction of the hydroxyl and other polar groups on the silica for the water molecules in these types of PCMs. Further, as set out in parent application Ser. No. 870,487, use of hydrophobic silica in combination with a non-polar PCM, e.g., an alkyl hydrocarbon, provides a solution to a phase separation problem otherwise encountered in a high humidity environment or on exposure of the dry powder to liquid water.

When water is used as the PCM, it has been found that while normal hydrophilic fumed silica can be used to form a dry powder with a PCM at the water/silica (65/35) concentration by weight, the preferred silica is a precipitated silica. The precipitated silicas are preferred over the fumed silicas for making the PCM/silica dry powders for several reasons. For example, the precipitated silicas sell for about ⅓ the price of the corresponding fumed silica, and the precipitated silicas have less tendency to tie up water molecules, thus providing higher thermal energy storage in water/silica dry powder. This dry powder remains soft and conformable above and below the melting temperature of water/ice. A water/silica dry powder is also low in cost and is non-burning. There are many applications for a water/silica dry powder in food servingware (to keep food cold) and in medical wraps (cold therapy). However, a preferred application is for heat protection for heat sensitive items, such as aircraft flight data recorders, and for preventing "brake fade" in automotive vehicles, aircraft and other vehicles.

As mentioned, it has been found that a very small size silica filler should be used as a matrix for the PCM. This silica filler has particle sizes on the order of about 0.005 to 0.025 microns in diameter and is capable of absorbing two to ten times its weight of liquid PCM. The silica filler is literally stirred into the liquid PCM at a temperature that is above the melting point of the PCM. At combinations of PCM/silica filler of 90/10–85/15 (weight) a gel composition is obtained. However, when mixed at 70/30 PCM/silica filler and at lower PCM content, a free-flowing powder is obtained that remains free flowing above and below the melting temperature of the PCM. This type of structure is especially desirable for hot and cold medical wrap applications, but is of interest in other applications such as for citrus tree wraps, tableware, building structures, soil admixtures, garments, blankets, quilts, flight data recorders, preventing brake fade, etc. In this instance, the preferred structure is an initially enclosed one for heat protection of flight data recorders, and for thermal protection of metal structures in buildings, ships and aircraft.

The addition range for the PCM is from about 75%–50% (by weight based upon total weight of the composite, i.e., silica-PCM mixture). For convenience in mixing, the dry silica is usually added to liquid PCM (i.e., PCM maintained at a temperature higher than its melting point). However, the reverse addition of PCM to silica can also be accomplished with suitable equipment to prevent aerosolization of the finely divided silica.

While a variety of different PCM materials may be used in the silica-PCM mixture when the solid-to-liquid transition is contemplated, the preferred PCM material of the present invention is a liquid-to-gas transition one. Because a liquid-to-gas transition is contemplated, the preferred phase change material is water because of its high thermal energy storage capacity. However, liquids other than water may be considered if a vaporization temperature higher or lower than that provided in the silica-water dry powders is necessary.

In accordance with the invention, a dry powder-like PCM-silica mix is provided that is particularly useful for thermal protection of heat sensitive items, such as aircraft flight data recorders, for thermal protection of metal structures in buildings, ships and aircraft, and for preventing "brake fade" in automobiles, trucks, buses and aircraft.

DETAILED DESCRIPTION OF THE PREFERRED EMBODIMENT

Figure 1:
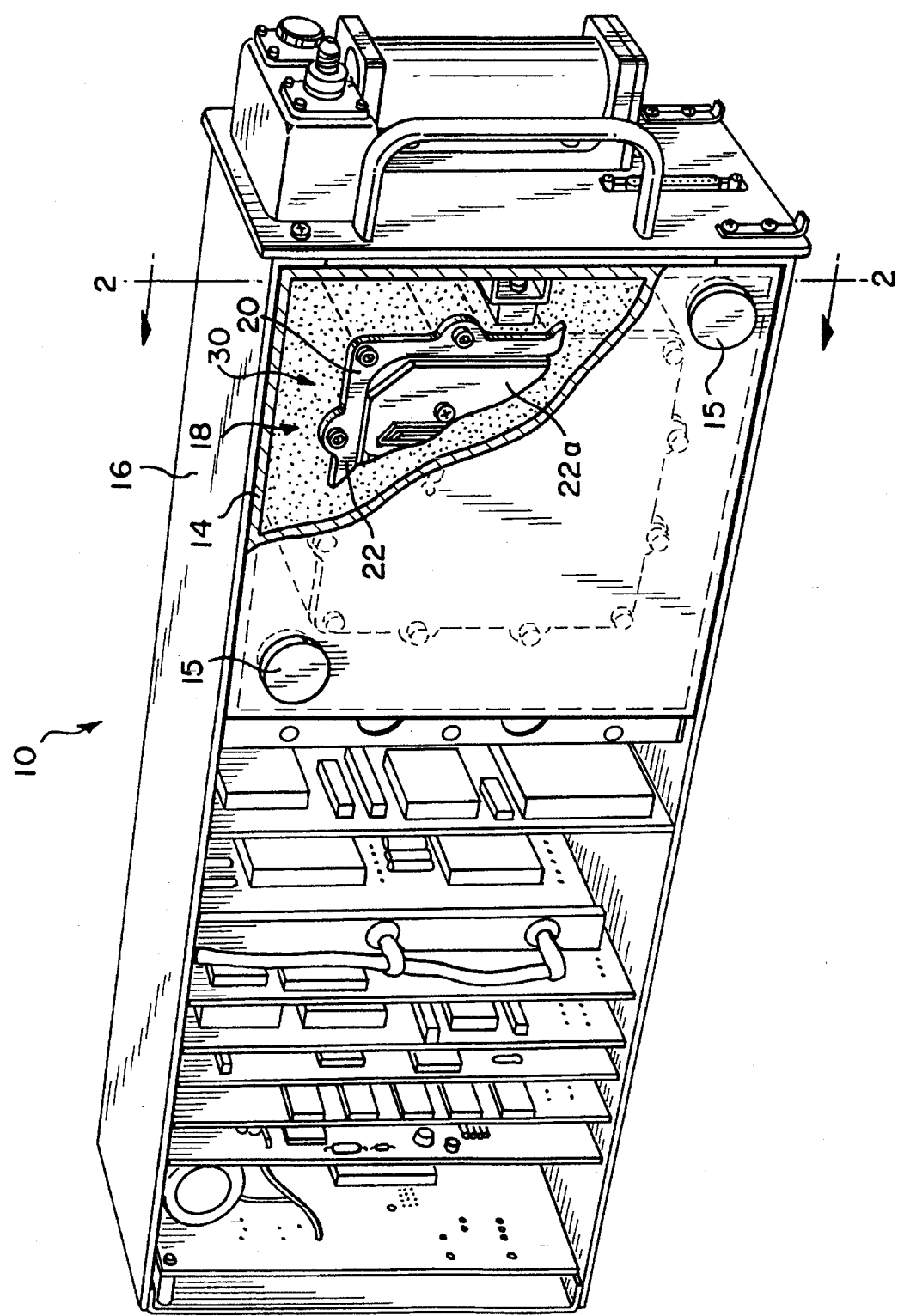
FIG. 1 is a perspective view, partially in section, of an aircraft flight data recorder with a side portion of its outer shell removed.

In accordance with the above, it is apparent that the ultrafine particle size silica provides a convenient carrier for the PCM. The fact that the PCM-silica powder mix readily conforms to different shapes is of benefit when the mix is used as an enclosed structure into which it is to be filled. The dry blend minimizes PCM leakage problems that may otherwise occur. Use of hydrophobic silica in combination with non-polar PCM provides solution to a phase separation problem otherwise encountered in high humidity environments or on exposure of the dry powder to liquid water.

As mentioned, the particle size of the silica is critical. Sub-micron, ultra fine particle size silicas on the order of about 0.005 to about 0.025 microns (in diameter) can be manually mixed in a solution of phase change material within a critical addition range. That is, the ultra-fine silica should be added to the phase change material to produce a mixture having about 70% PCM (weight PCM based on total weight of PCM and silica in mix) or less. If more than about 70% of the PCM is added, a gel-like mixture is provided. However, at about 70/30PCM:silica, a free-flowing powder is obtained that remains free-flowing both above and below the melting temperature of the PCM. For optimum cold conformability, a composition of PCM/silica of 65/35 is preferred.

As set forth in related application Ser. No. 462,365, sub-micron particle size silicas made by either of two different processes (i.e. either fumed silica made by hydrolysis of silicon tetrachloride vapor in a hydrogen/oxygen flame or precipitated silica made from an alkaline silicate such as sodium silicate that is precipitated with a mineral acid or metal salt) may be used in the powder mix. However, as set forth in parent application Ser. No. 870,487, either a precipitated silica or a surface treated precipitated silica is preferred depending on the PCM used and the use to which the dry powder is put.

Thus a preferred silica is a precipitated hydrophilic silica having a particle size of 0.005 to 0.025 microns and a surface area of 100 m² per gram or more. An example is ABS silica from PPG Industries of Pittsburgh, Pa., which is a normal, hydrophilic silica with a surface area of 150 m²/gram and a particle size of about 0.022 microns.

Alternatively, the preferred silica is a precipitated hydrophilic silica of the same type that has been further surface treated to render it less hydrophilic, partially hydrophobic, or hydrophobic. Preferably the silica is treated with 1–15 pph (parts per hundred by weight) of a silane coupling agent such as dimethyldichlorosilane or silicone resin. The preferred degree of hydrophobic character depends on the type of PCM being used. For example, with water as the phase change material, the silica should be completely hydrophilic or only slightly (i.e. around 1 pph) waterproofed by surface treatment. When the phase change material is a quaternary ammonium halide or a salt hydrate or when a non-water PC/M/silica dry powder is to be used in a moist environment (i.e. where phase separation can occur quickly as the silica preferentially absorbs water and absorbs the non-water PCM), then a less hydrophilic, partially hydrophobic, or hydrophobic silica is preferred.

Other than the above-mentioned preferences on the types of silica used with certain PCM's and depending on certain uses to which the dry powder is put, all of the silicas mentioned in related application Ser. No. 462,365 may be used. Likewise, all of the PCM's mentioned in related application Ser. No. 462,365 may be used.

In the '365 application, crystalline alkyl hydrocarbons having a chain length of $C_{14}$ and greater where indicated to be the preferred PCM for many situations. While such alkyl hydrocarbons remain preferred for a number of situations, recently water/silica dry powders have gained emphasis for a number of uses including ice packs (in place of cold gel packs), food servingware (to keep cold food cold) and in medical wraps (cold therapy), as disclosed in parent application Ser. No. 870,487. A water/silica dry powder of the type disclosed therein has an excellent capability of storing and releasing thermal energy within the temperature range preferred for ice packs, food servingware and medical wraps, is the lowest cost dry powder, and remains soft and conformable above and below the melting temperature of water/ice. The water/silica dry powder also has a high heat of vaporization enabling it to provide significant thermal protection for heat sensitive items, such as aircraft flight data recorders, safes, files and similar enclosures for valuables, as is preferred in this instance. The water/silica dry powder may also be used to prevent "brake fade" in auto and aircraft brake systems.

As to the other PCM's that may be used, preferred are those polar organic compounds that undergo a liquid-to-gas transition with high heat of vaporization and condensation such as ethylene glycol, combinations of water and ethylene glycol, glycerol, glycerol-water, glycerol-glycol, glycerol-glycol-water, methanol, dimethylformamide, and like materials.

In some instances, however, a solid-to-liquid transition material may be used such as water, salt hydrates, quaternary ammonium halide clathrates, linear alkyl hydrocarbons, fatty acids, alcohols and esters, glycerine, pentaerythritol, pentaglycerine, neopentylglycol, and polyethylene glycol, which are described in parent application Ser. No. 870,487.

The silica-PCM mix may also be enhanced by the use of an antioxidant in the formulation. Typically, the antioxidant will be needed only when the crystalline alkyl hydrocarbon PCM or a polar organic PCM such as ethylene glycol, polyethyleneglycol or glycerine is employed. The antioxidants should be added, when used, in an amount of from 0–5% (weight) and preferably in an amount of from 0.1–1% (weight) based on the weight of the PCM. Exemplary antioxidants include the well-known hindered phenol materials and aromatic amines. Preferred antioxidants include BHA (butylated hydroxy anisole), BHT (butylated hydroxytoluene) Santowhite crystals (i.e., 4,4'-thiobis(6-tert-butyl-m-cresol) and Santowhite powder (i.e., 4,4'-isopropylidene bis(6-tert-butyl-m-cresol). The Santowhite products are available from Monsanto.

It is to be understood that thermal insulation materials such as polyurethane or polystyrene foam are desirably used to surround the shrouded PCM/silica composites in order to minimize undesirable heat loss or gain from the environment. In that case, a layer of such thermal insulation would be provided so as to minimize heat loss or gain.

Figure 2:
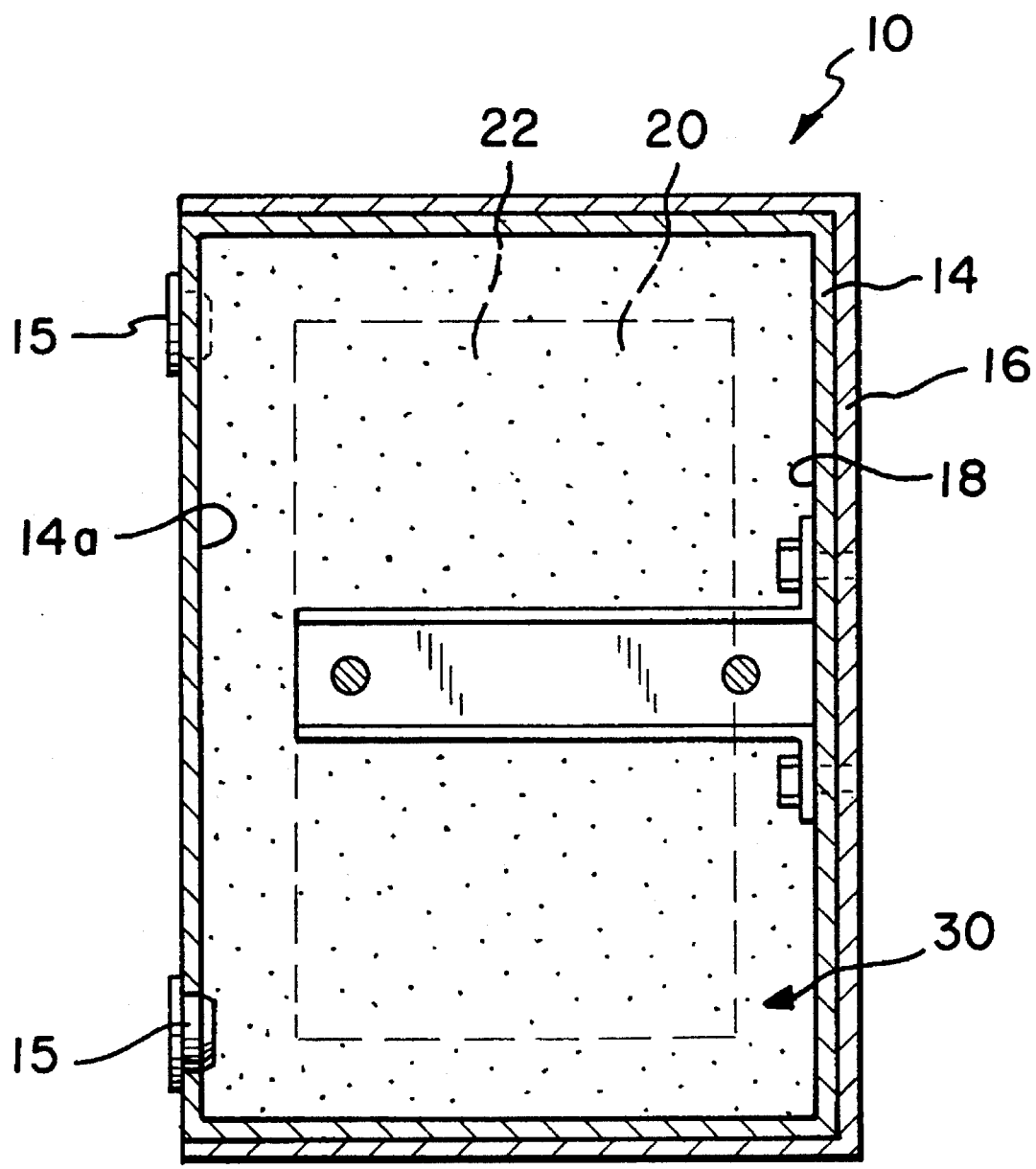
FIG. 2 is a cross-sectional view taken generally along line 2—2 in FIG. 1.

A particular application involving use of the silica/PCM mixture to thermally protect a heat sensitive item will now be described. In FIGS. 1 and 2, a flight data recorder 10 is shown having an internal memory unit 20 surrounded by a silica/PCM dry powder mixture 30. The memory unit 20 comprises a housing 22 having an inner cavity (not shown) in which one or more memory devices (not shown) are contained. As is known in the art, the memory devices store and preserve flight data. In the event that the aircraft in which the recorder 10 is employed is involved in a crash or other mishap, the flight data is retrieved from the memory devices and reviewed to aid in the determination of the cause of the mishap. The flight data recorder 10 may alternatively comprise a cockpit voice recorder having storage means for recording voice communications originating in the aircraft cockpit.

The memory unit 20 is secured within a protective casing 14 which, in turn, is secured within an outer shell 16 of the recorder 10. The silica/PCM dry powder 30 is housed with a chamber 18, defined by the inner surface 14a of the protective casing 14 and the outer surface 22a of the housing 22. A plurality of blow-out vents or plugs 15 are provided in the protective casing 14. The vents 15 release at a predetermined chamber pressure level to provide passages for the vaporized phase change material to exit the chamber 18.

Preferably, the phase change material used in the silica/PCM dry powder 30 is distilled or deionized water which is filtered to remove any particulate impurities. The water should be present in an amount from about 63% to about 65% by weight of the dry powder 30. The silica may be the previously discussed precipitated hydrophilic silica (e.g., ABS silica from PPG Industries of Pittsburgh, Pa.), and is preferably present in an amount from about 37% to about 35% by weight of the dry powder 30.

A dye, such as a royal blue dye sold by Bunge Foods, Bradley, Illinois, may be added to the silica/PCM dry powder 30 (~0.1% by weight of the dry powder mixture 30). In the case of an aircraft mishap, after the PCM has vaporized and left the chamber 18 via the vents 15, the silica remains and provides an effective layer of insulation through establishing a still air environment that reduces the rate of heat transfer across the chamber 18. With little or no PCM left in the chamber 18, the temperature of the silica will begin to increase from the outer portion of the chamber 18 (adjacent inner wall 14a), to the inner portion thereof. This will cause the dye-to degrade and fade to a white color. Thus, the faded silica provides an indication as to how far inward the high temperature boundary has progressed through the silica.

It is further contemplated by the present invention that a lining of insulation material (not shown), such as glass wool, may be provided between the inner surface 14a of the protective casing 14 and the silica/PCM dry powder mix 30.

Advantages resulting from use of the silica/PCM dry powder mix 30 in the recorder 10 include: significant thermal protection for the memory unit 20 due to the high heat of vaporization of the water PCM; no free water is present that could leak from the chamber 18; the mix 30 experiences little or no volume change when it is subjected to low temperatures; the silica/PCM mix 30 can be easily poured into the chamber 18; and, after the water has vaporized, the silica remains and serves as an effective layer of insulation that reduces the rate of heat transfer across the chamber 18. Additionally, the water/silica dry powder acts as an effective impact absorber resulting from its soft, conformable structure.

If a particular application requires a vaporization temperature higher than that provided by the silica/water dry powder, ethylene glycol, combinations of water and ethylene glycol, or dimethylformamide may be used as the PCM. If a vaporization temperature lower than that provided by the silica/water powder is desired, methanol, ethanol, etc., may be used as the PCM.

It is additionally contemplated by the present invention that, by increasing or decreasing the pressure within the sealed chamber housing the silica/PCM powder, the vaporization temperature for the phase change material can be altered, thereby allowing temperature control at higher or lower temperatures.

The thermal protection provided by the water/silica dry powder may also be advantageously utilized in protecting safes, files, and similar enclosures for valuables from destruction in a fire. In such an application, the water/silica dry powder is contained in an annular space located either inside or outside of the container. The container is preferably formed from a fire resistant material, e.g., a high melting point metal. The annular space is sealed prior to "use" to prevent gradual loss of water vapor over a long period of time. The container is provided with pressure release valves to allow escape of steam (to remove heat) when the container is exposed to fire. As will be understood by those skilled in the art, other types of enclosures or structures that could benefit from the thermal protection of the water/silica system of the present invention may be used without departing from the scope of the invention.

It is also contemplated that the silica/PCM powder may be used for thermal protection of metal structures in buildings, ships and aircraft.

An additional application involving use of the PCM/silica mixture to prevent vehicle "brake fade" will now be described. "Brake fade" occurs in a brake system when heat is generated faster than it can be dissipated. For example, in a caliper disc brake system, if an excessive amount of heat is generated and the temperature of a brake pad in that system increases sufficiently, the resin binder in the pad will degrade resulting in an oily material appearing at the interface between the brake pad and the disk. This oily material acts as a lubricant and hence prevents proper functioning of the brake system.

Figure 3:
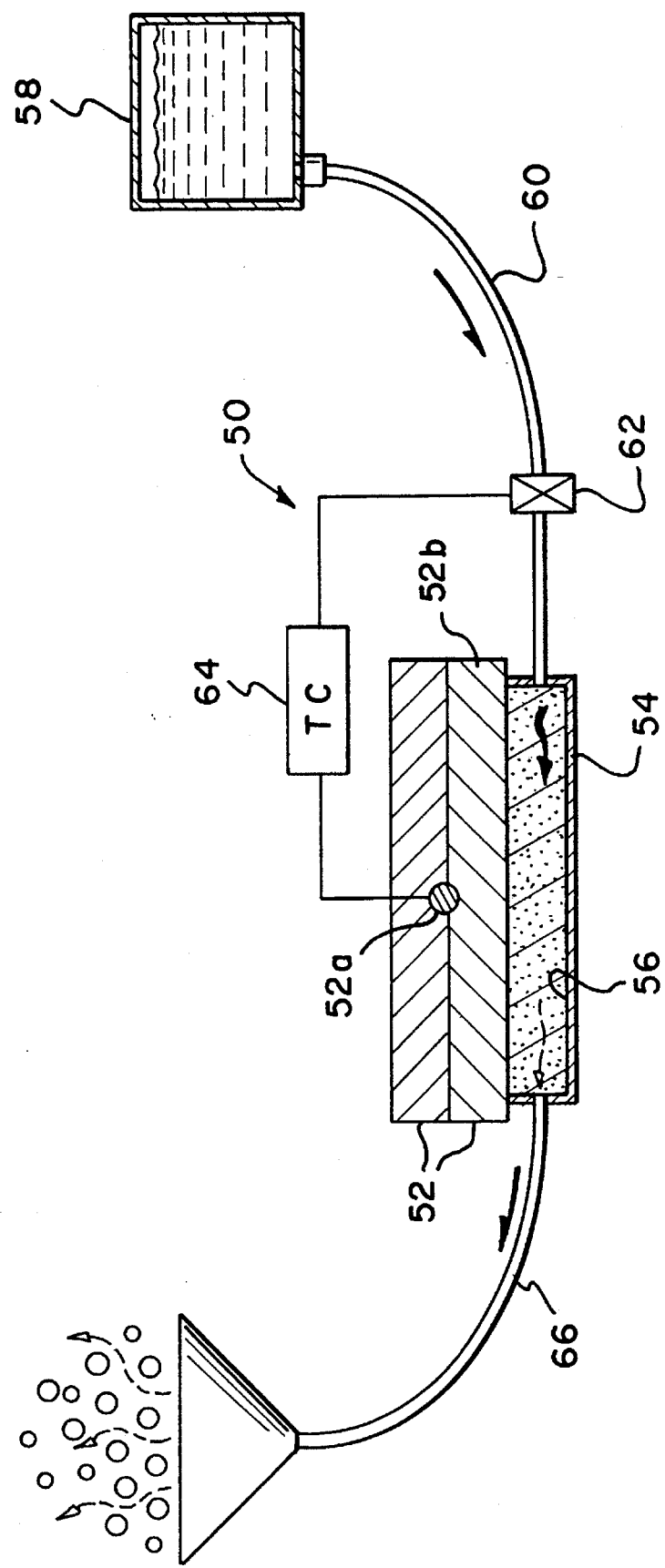
FIG. 3 is a schematic illustration of a water/silica dry powder system associated with a brake pad for preventing "brake fade."

In FIG. 3, a heat dissipation system 50 is illustrated which functions to absorb heat from a brake pad 52. The system 50 includes a housing 54 having an inner evaporating chamber 56 containing silica dry powder (e.g., ABS silica from PPG Industries). In the illustrated embodiment, the chamber 56 communicates with a fluid resupply source 58 through a fluid line 60 and an electric solenoid control valve 62. In motor vehicles, the fluid source 58 can conveniently comprise a windshield washer fluid reservoir. An advantage to using this resupply source is that windshield washer fluid normally contains a freezing point depressant that ensures that it will be a liquid at below 0° C. temperatures.

The brake pad 52 is provided with a temperature sensor 52a, such as a thermocouple (e.g., iron-constant an, copper-constant an, and chromel-p-alumel), which is attached securely to a metal portion 52b of the brake pad 52. When the thermocouple 52a is heated, an electric signal is generated that varies linearly with temperature. The electric signal is passed to a temperature controller 64 which, in turn, amplifies and compares the signal to a threshold value to control the opening and closing of the electric solenoid control valve 62.

As heat is generated upon the pad 52 engaging a metal disk (not shown) during braking, the water or other fluid within the chamber 56 absorbs heat and is converted to water or other vapor (545,000 calories of energy are absorbed for every one liter of water evaporated). The vaporized fluid is emitted to atmosphere through vent line 66. Accordingly, by evaporating the PCM in the chamber 54, a substantial amount of heat is absorbed from the pad 52, thereby preventing brake fade. This system 50 may be used in vehicles including automobiles, trucks, buses, trains and aircraft.

In an alternative embodiment, the thermocouple is replaced by a bimetallic spring attached to the metal portion 52b of the brake pad 52. When the temperature rises above some predefined value, e.g., 100° C., the bimetallic spring closes a set of electric contact points to supply current to open the solenoid valve 62. When the temperature falls below the predefined value, the contact points open in response to movement of the spring causing the valve 62 to close and shut off the supply of PCM to the cheer 56.

It is further contemplated, that the housing 54 may be used without a resupply source. Such a system, however, would provide cooling for only a limited number of occasions where brake fade would otherwise be encountered.

In order that the invention may be more readily understood, reference is made to the following examples, which are intended to be illustrative of the invention, but are not intended to be limiting in scope.

EXAMPLE 1

This example illustrates the general laboratory procedure for preparing a water/silica dry powder thermal energy storage composition. One thousand grams of distilled water was placed into a mixing tray having the dimensions of about 14"×18"×5". The tray preferably comprises stainless steel, although porcelain or plastic trays may also be suitable. Since water is in the liquid state at room temperature it was not necessary to apply any heat to the mixing tray.

From a preweighed lot, a commercially available precipitated hydrophilic silica from PPG Industries of Pittsburgh, Pa. (ABS silica) having a surface area of 150 $m^2$/gram and an ultimate particle size of about 0.022 microns was incrementally added to the distilled water with a putty knife while mixing and stirring. The ABS silica was readily wetted by the water PCM, and an increase in the viscosity of the water was noted after a water/silica 90/10 composition was achieved. Further addition of silica resulted in a loose gel at about water/silica 85/15 composition, and a stiff gel at about water/silica 80/20. The conversion of the stiff gel to the dry powder was achieved by adding more ABS silica and mixing the silica into the gel particles with a putty knife. Care must be taken to break up the gel particles as completely as possible by intensive manual mixing. A dry powder was obtained when sufficient ABS silica has been added to bring the composition to water/silica 70/30 or 60/40 range. Thus for a water/silica dry powder the preferred weight % of water is 60–70%. Optionally, after the dry powder has been formed, it may be screened through a 20 mesh screen to remove any large gel particles. These can be broken up manually and remixed into the balance of the dry powder.

Tests that are then run on the dry powder are apparent density, thermal energy storage, and cold conformability (the ability to retain the loose powder structure at a temperature below the freezing temperature of the PCM). The apparent density of the dry powder should be about 0.5 gm/cc. The thermal energy storage should be near that calculated from the thermal energy storage of the neat (100%) PCM, and multiplied by percent PCM in the dry powder. The conformable property is determined by placing the material in a freezer overnight and determining if the sample retains the free flowing characteristics that it has at ambient temperature.

An analysis of the thermal energy storage properties of water/ABS silica dry powder was conducted using a differential scanning calorimeter (DSC). In this test, a small sample was heated at a controlled rate (e.g., 2° C./minute) and the energy required to maintain the constant rate of temperature was monitored in comparison with a control blank. The extra electrical energy required to maintain the constant rate of heating and cooling becomes a direct measure of the energy of melting and freezing and is usually expressed in calories/grams. The exact location of the melting and freezing temperature is simultaneously located in this test, and the extent of supercooling (if present) is also measured. A differential scanning calorimeter analysis was run on a sample of distilled water/ABS silica dry powder PCM at a heating and cooling rate of 2° C./minute. The DSC data is shown in Table 1 below.

An application test of the water/ABS silica dry powder was also performed wherein the time versus temperature of 300 grams samples of water/ABS silica dry powder, and a 15 carbon alkyl hydrocarbon from EXXON of Houston, Texas (NP-15)/ABS silica dry powder, and a commercial water gel cold pack were measured. Samples of the three cold packs were placed on a counter top, thermocouples placed underneath each, and the time versus temperature recorded. It was readily apparent that the water/ABS silica dry powder, and the NP-15/ABS silica dry powder both provide a plateau of stable temperature near the respective temperatures of the Tc for more than 2 hours. On the other hand, the water gel had no temperature plateau and only showed a continuing thermocline from 32° F. toward room temperature.

EXAMPLE 2

Five types of precipitated silicas (all of which are commercially available from PPG Industries of Pittsburgh, Pa.) were selected that differed in particle size, surface area, size and amount of agglomerates, and surface treatment (to reduce hygroscopicity). The basic properties and characteristics of each of these silicas are summarized below in Table 2.

TABLE 1

| Material | Tm °C. | Tc °C. | Tm − Tc °C. | AHf Cal/gm | AHc Cal/gm |
|---|---|---|---|---|---|
| $H_2O$/ABS (63/37) | 0.91 | −3.47 | 4.38 | 40.81 | 38.26 |
| $H_2O$/ABS (63/37) | 0.88 | −3.47 | 4.35 | 37.75 | 34.65 |

TABLE 2

| Type of Silica | ABS | BXS-318 | LXR-075 | T-690 | 532EP |
|---|---|---|---|---|---|
| 1. D.B.P. Oil Absorption (cc/100 9m) | 300 | 295 | 345 | 220 | 185 |
| 2. Surface Area ($m^2$/gram) | 150 | 126 | 145 | 170 | 60 |
| 3. Ultimate Particle Size (nm) | 22 | 22 | ~22 | 19 | 46 |

TABLE 2-continued

| Type of Silica | ABS | BXS-318 | LXR-075 | T-690 | 532EP |
|---|---|---|---|---|---|
| 4. Colter Counter Agglomerate Size (um) | 22 | 25 | 22 | 1.3 | 7 |
| 5. pH (5% $H_2O$ Slurry) | 7 | NA | 7 | 7 | 8 |
| 6. Bulk Density (lbs/ft$^3$) | 8 | 7 | 8 | 4 | 10 |
| 7. Free Water (%) | 4 | ~3 | 4 | 6 | 5 |
| 8. NaCl (%) | .03 | .03 | .03 | .03 | .03 |
| 9. $Na_2SO_4$ (%) | 1.25 | 1.25 | 1.25 | 1.60 | 1.25 |
| 10. Water Proofing Surface Treatment | No | Yes (Treated with silicone resin to confer some degree of hydrophobicity) | No | No | No |

Five water/silica dry powders were prepared using the five silicas set out in Table 2. Each of the powders, except for the water/532EP powder, included silica particles in an amount of about 35% by weight of the powder mix. The water/532EP powder included silica particles in an amount of 39.4% by weight of the powder mix.

Each of the five water/silica dry powders was analyzed for heat of vaporization by differential scanning calorimetry (DSC). The DSC analysis is discussed above in Example 1. The amount of water released as steam for each of the powders was determined by thermogravimetric analysis (TGA). This test determines evaporative weight loss and should be run over the temperature range of about 25° C. to about 250° C. at a heating rate of about 10° C./minute. The apparent density, cold conformability and the amount of silica required to initially convert each of the samples to the dry powder stage were also determined. The results are summarized below in Table 3.

As indicated in Table 3, the water/BXS-318 powder had the highest heat of vaporization (335 cal/gram), while the remaining four dry powders each had about the same total heat of vaporization (322 cal/gram). The lowest temperature for the maximum rate of evaporation was obtained in the water/T-690 dry powder (70.65° C.). The other four dry powders had maximums in rate of evaporation at temperatures near 80° C. The highest weight loss % (63.72%) was observed in the water/T-690 dry powder. The lowest weight loss % (56.76%) was found in the water/532EP dry powder, which powder also contained less water initially.

The water/532EP powder required the greatest amount of silica (39.4%) before a dry powder was initially obtained. The water/ABS and water/LXR-075 powders required the least amount of silica (26.3% and 26.5%, respectively) before a dry powder was initially obtained.

TABLE 3

| | $H_2O$/ABS | $H_2O$/BXS-318 | $H_2O$/LXR-075 | $H_2O$/T-690 | $H_2O$/532EP |
|---|---|---|---|---|---|
| 1. DSC | | | | | |
| T Max °C. | 85.39 | 91.64 | 78.75 | 85.88 | 85.39 |
| T Start °C. | 28.02 | 22.36 | 23.36 | 26.55 | 28.12 |
| T Stop °C. | 108.29 | 110.94 | 99.33 | 103.68 | 108.29 |
| ΔHI cal/gram | 322.10 | 335.01 | 322.34 | 321.39 | 322.1 |
| 2. TGA | | | | | |
| T Max °C. | 81.44 | 79.42 | 80.00 | 70.67 | 83.46 |
| T Start °C. | 28.45 | 30.64 | 29.86 | 30.64 | 28.87 |
| T Stop °C. | 140.00 | 140.00 | 140.00 | 140.00 | 140.00 |
| Wt. Loss % | 61.47 | 61.50 | 57.40 | 63.72 | 56.76 |
| Residue % | 38.33 | 38.24 | 42.35 | 36.20 | 43.00 |
| 3. APPARENT DENSITY grams/cc | .547 | .565 | .510 | .586 | .640 |
| 4. Weight % SILICA TO DRY POWDER % | 26.3 | 30.0 | 26.5 | 34.8 | 39.4 |
| 5. COLD CONFORMITY | 3 | 4 | 3 | 6 | 7 |

The cold conformity of the dry powders was rated after overnight storage in a deep freeze. Conformability was rated on a scale of 1 to 10, with 1 being a free flowing powder, and 10 being a hard ice. The water/ABS and water/LXR-075 powders performed best in this regard.

Because the water/ABS mix had the highest water absorbing capacity (as shown by having the lowest weight % silica to dry powder), had acceptable heat storage capacity (322 cal/gram), and had the lowest cost, it is believed to be the best water/silica mix for use in a flight data recorder to thermally protect the recorder's internal memory unit.

EXAMPLE 3

Glycol/ABS silica and glycol-water/ABS dry powder composites were prepared (65/35 PCM/ABS). Each was analyzed for heat of vaporization by differential scanning calorimetry (DSC). Each was further analyzed by thermogravimetric analysis (TGA) to determine the amount of PCM released. The amount of silica required to convert each sample initially to the dry powder stage was also determined. The results are summarized below in Table 4.

TABLE 4

|  | Ethylene Glycol/ABS | Ethylene Glycol-water (75/25)/ABS |
|---|---|---|
| 1. DSC |  |  |
| T Max °C. | 165.00 | 164.18 |
| T Start °C. | 13.97 | 19.63 |
| T Stop °C. | 174.40 | 172.10 |
| ΔHl cal/gram | 220.78 | 210.9 |
| 2. TGA |  |  |
| T Max °C. | 140.0 | 130.72 |
| T Start °C. | 42.05 | 32.19 |
| T Stop °C. | 165.0 | 160.0 |
| Wt. Loss % | 74.83 | 73.55 |
| Residue % | 25.02 | 26.13 |
| 3. SILICA TO DRY POWDER % | 26.02 | 25.89 |

As indicated in Table 4, the glycol/ABS silica powder had a heat of evaporation of 220.78 cal/g, while the glycol-water/ABS silica powder had a heat of evaporation of 210.9 cal/g. Thus, the heat of evaporation values for both powders were well below the heat of evaporation values for the water/silica powders set out in Example 2.

The glycol/ABS silica powder had a maximum in rate of evaporation at a temperature of 140° C., while the glycol-water/ABS silica powder had a maximum in rate of evaporation at a temperature of 130.72° C. Also, both powders had similar weight loss percentages (about 74%).

While certain representative embodiments and details have been shown for purposes of illustrating the invention, it will be apparent to those skilled in the art that various changes in the methods and apparatus disclosed herein may be made without departing from the scope of the invention, which is defined in the appended claims.

What is claimed is:

1. An enclosure for thermally protecting a heat sensitive item from high temperatures, said enclosure comprising:
   a housing including an inner cavity for containing said heat sensitive item;
   an outer casing enclosing at least a portion of said housing, said outer casing and said portion of said housing defining a chamber therebetween; and
   a mixture of a phase change material and finely divided silica particles disposed within said chamber adjacent to said portion of said housing providing significant thermal protection for said heat sensitive item said phase change material selected from the group consisting of polar organic compounds that undergo a liquid-to-gas transition with high heat of vaporization and condensation, combinations thereof, and combinations of water and polar organic compounds that undergo a liquid-to-gas transition with high heat of vaporization and condensation.

2. An enclosure as set forth in claim 1, wherein said phase change material is selected from the group consisting of ethylene glycol, combinations of water and ethylene glycol, glycerol, glycerol-water, glycerol-glycol, glycerol-glycol-water, methanol, and dimethylformamide.

3. An enclosure as set forth in claim 1, wherein said phase change material is present in an amount from about 60% to about 70% by weight of said mixture.

4. An enclosure as set forth in claim 1, wherein said silica particles are present in an amount from about 30% to about 40% by weight of said mixture.

5. An enclosure as set forth in claim 1, wherein said phase change material is present in an amount of about 64% by weight of said mixture and said silica particles are present in an amount of about 36% by weight of said mixture.

6. An enclosure as set forth in claim 1, further comprising at least one blow-out vent located in said outer casing for opening at a predetermined chamber pressure level to provide a passage for said phase change material to exit said chamber.

7. An enclosure as set forth in claim 1, further comprising a layer of insulating material provided within said chamber.

8. An enclosure as set forth in claim 7, wherein said insulating material is located between the inner surface of said outer casing and said mixture.

9. An enclosure as set forth in claim 7, wherein said insulating material comprises glass wool.

10. An enclosure as set forth in claim 1, wherein said silica particles have a surface area of between about 120 m²/g and 170 m²/g.

11. An enclosure as set forth in claim 1, wherein said silica particles have particle sizes of about 0.019 to about 0.025 microns.

12. An enclosure as set forth in claim 1, wherein said housing is entirely enclosed within said outer casing.

13. An enclosure as set forth in claim 1, wherein said heat sensitive item is a memory device for storing data which is to be recovered from said memory device following exposure of said enclosure to high temperatures.

14. A method for thermally protecting heat sensitive item from high temperatures comprising the steps of:
   providing a mixture of phase change material and finely divided silica particles said phase change material being selected from the group consisting of polar organic compounds that undergo a liquid-to-gas transition with high heat of vaporization and condensation, combinations thereof, and combinations of water and polar organic compounds that undergo a liquid-to-gas transition with high heat vaporization and condensation;
   locating said mixture adjacent to said heat sensitive item to protect said heat sensitive item from high temperatures.

15. A method as set forth in claim 14, wherein said phase change material is selected from the group consisting of ethylene glycol, combinations of water and ethylene glycol, glycerol, glycerol-water, glycerol-glycol, glycerol-glycol-water, methanol, and dimethylformamide.

16. A method as set forth in claim 14, wherein said phase change material is present in an amount from about 60% to about 70% by weight of said mixture.

17. A method as set forth in claim 14, wherein said step of locating said mixture adjacent to at least a portion of said heat sensitive item comprises the step of encapsulating said heat sensitive item in said mixture.

18. A method as set forth in claim 14, wherein said step of providing a mixture of phase change material and finely divided silica particles comprises the step of selecting a phase change material that vaporizes at a temperature below a temperature which might cause harm to said heat sensitive item.

19. A system for absorbing heat from a heat sensitive item comprising:

a housing positioned adjacent to said item and including an inner chamber; and a mixture of a phase change material and finely divided silica particles disposed within said chamber for absorbing heat from said heat sensitive item said phase change material being selected from the group consisting of polar organic compounds that undergo a liquid-to-gas transition with high heat of vaporization and condensation, combinations thereof, and combinations of water and polar organic compounds that undergo a liquid-to-gas transition with high heat of vaporization and condensation.

20. A system as set forth in claim 19, wherein said heat sensitive item comprises a brake pad.

* * * * *